US005558083A

United States Patent [19]
Bathe et al.

[11] Patent Number: 5,558,083
[45] Date of Patent: Sep. 24, 1996

[54] NITRIC OXIDE DELIVERY SYSTEM

[75] Inventors: Duncan P. L. Bathe, Madison; Thomas S. Kohlmann, McFarland; John R. Pinkert, Madison; Robert Q. Tham, Middleton, all of Wis.

[73] Assignee: Ohmeda Inc., Liberty Corner, N.J.

[21] Appl. No.: 156,175

[22] Filed: Nov. 22, 1993

[51] Int. Cl.$^6$ ................................................. A61M 15/00
[52] U.S. Cl. .......................... 128/203.12; 128/203.14; 128/203.25
[58] Field of Search .................. 128/202.22, 203.12, 128/203.14, 203.25, 205.23

[56]       References Cited

U.S. PATENT DOCUMENTS

| | | | |
|---|---|---|---|
| 4,127,121 | 11/1978 | Westenskow et al. | 128/203.14 |
| 4,191,952 | 3/1980 | Schreiber et al. | 128/203.14 |
| 4,328,823 | 5/1982 | Schreiber | 128/203.14 |
| 4,336,798 | 6/1982 | Beran | 128/205.23 |
| 4,345,612 | 8/1982 | Koni et al. | 128/203.14 |
| 4,442,856 | 4/1984 | Betz | 128/202.22 |
| 4,611,590 | 9/1986 | Ryschka et al. | 128/203.14 |
| 4,770,168 | 9/1988 | Rusz et al. | 128/203.14 |
| 5,159,924 | 11/1992 | Cegielski et al. | 128/203.25 |
| 5,197,462 | 3/1993 | Falb et al. | 128/203.14 |

FOREIGN PATENT DOCUMENTS

| | | |
|---|---|---|
| 2121384 | of 1994 | Canada. |
| 4325319 | of 1994 | Germany. |
| WO92/11052 | of 1992 | WIPO. |
| WO92/10228 | of 1992 | WIPO. |

OTHER PUBLICATIONS

The Journal of Clinical Investigation, vol. 90, No. 2, Aug. 1992, pp. 421–428.

Primary Examiner—Aaron J. Lewis
Attorney, Agent, or Firm—Roger M. Rathbun; R. Hain Swope; Larry R. Cassett

[57]       ABSTRACT

A nitric oxide delivery system that is useable with any of a variety of gas delivery systems that provide breathing gas to a patient. The system detects the flow of gas delivered from the gas delivery system at various times and calculates the flow of a stream of nitric oxide in a diluent gas from a gas control valve. The flow of gas from the gas delivery system and the flow established from the flow control valve create a mixture having the desired concentration of nitric oxide for the patient.

The system does not have to interrogate the particular gas delivery system being used but is an independent system that can be used with various flows, flow profiles and the like from gas delivery systems.

27 Claims, 2 Drawing Sheets

NITRIC OXIDE DELIVERY SYSTEM

BACKGROUND OF THE INVENTION

The administration of inhaled nitric oxide (NO) to patients is currently being investigated for its therapeutic effect. The use of NO has a vasodilatory effect on such patients and is particularly of importance in the case of newborns having persistent pulmonary hypertension. In such cases, the administration of NO has significantly increased the oxygen saturation in such infants.

The function of the administration of NO has been fairly widely published and typical articles appeared in The Lancet, Vol. 340, October 1992 at pages 818–820 entitled "Inhaled Nitric Oxide in Persistent Pulmonary Hypertension of the Newborn" and "Low-dose Inhalational Nitric Oxide in Persistent Pulmonary Hypertension of the Newborn" and in Anesthesiology, Vol. 78, pgs. 413–416 (1993), entitled "Inhaled NO—the past, the present and the future".

The actual administration of NO is generally carried out by its introduction into the patient as a gas along with other normal inhalation gases given to breathe the patient. Such commercially available supplies are provided in cylinders under pressure and may be at pressures of about 2000 psi and consist of a mixture of NO in nitrogen with a concentration of NO of between about 800–2000 ppm. As such, therefore, some means must be used to reduce the pressure of the supply to acceptable levels for a patient and also to very precisely meter the amount of the NO and nitrogen mixture so that the desired concentration of NO is actually administered to the patient. Such administration must also be added in sympathy with the respiration pattern of the patient.

The concentration administered to a patient will vary according to the patient and the need for the therapy but will generally include concentrations at or lower than 150 ppm. There is, of course, a need for that concentration to be precisely metered to the patient since an excess of NO can be harmful to the patient. In addition, the administration must be efficient in a timely manner in that NO is oxidized in the presence of oxygen to nitrogen dioxide and which is a toxic compound. Therefore, care in its administration is paramount.

Current known methods of such administration, therefore have been limited somewhat to clinical situations where attending personnel are qualified from a technical sense to control the mixing and administration of the NO to a patient. Such methods have included the use of a forced ventilation device, such as a mechanical ventilator where a varying flow os breathing gas is delivered to the patient as well as gas blenders or proportioners that supply a continuous flow of the breathing gas to the patient to which NO has been added.

In the former case, the use of a ventilator is constrained in that the user must know the precise flow from the ventilator and then the amount of NO to be added is determined on a case-to-case and moment-to-moment basis. Furthermore, the flow profile in forced ventilation varies continuously thereby making it impossible to track the flow manually. In the use of the latter gas blenders, the introduction of the NO containing nitrogen has been accomplished through the use of hand adjustment of the gas proportioner in accordance with a monitor that reads the concentration of NO being administered to the patient. Thus the actual concentration is continuously being adjusted by the user in accordance with the ongoing conditions of the apparatus providing the breathing mixture.

While such modes of providing a known concentration of NO to the patient may be acceptable from a closely controlled and monitored clinical setting, it is advantageous to have a system that could be used with various means of providing the breathing gas, whether by mechanical means such as a ventilator, or by the use of a gas proportioner and which could automatically adjust for that particular equipment and assure the user that the desired, proper concentration of NO is being administered to the patient.

SUMMARY OF THE INVENTION

In accordance with the present invention, there is provided a nitric oxide delivery system that is useable with various means of administering the NO, including the use of any mechanically assisted ventilation and ventilatory pattern, such as a ventilator or with spontaneous ventilation where the NO is introduced by means of a gas proportioning device that provides a continuous flow to the patient. The invention includes a flow transducer that senses the flow of gas from the gas delivery system and uses that information with a selective algorithm to provide an operator selectable concentration of NO to the patient. As used herein, the term gas delivery system is intended to include various types of gas proportioning devices, gas mixers and various types of mechanical ventilators used to provide breathing gas to a patient and may include an anesthesia machine, or manual bag, used with a patient undergoing an operation and which has a fresh gas supply.

In the preferred embodiment, a CPU obtains information from the flow transducer and from an input device that allows the user to select the desired concentration of NO to be delivered to the patient and calculates the flow of NO/nitrogen to obtain that selected concentration. It will be noted, however, that while a CPU is preferred, the signal processing needed by this system can readily be accomplished through the use of alternate technologies, such as analog or digital circuitry, fluidic circuits, optical means or mechanical components. The term "signal processing means" is intended to encompass the variety of ways that may be utilized to carry out the various signal processing functions to operate the subject NO delivery system.

Accordingly, the present system can be used with precision with various gas delivery systems, including ventilators of different manufacturers operating with diverse ventilatory patterns without the need to calculate output from the ventilator, to interrogate the gas delivery means, or to regulate the concentration manually. The user is thus free to concentrate on other procedures that will improve the patient.

By use of the CPU, various algorithms may be stored and used as appropriate. For example, there may be one algorithm that is used to obtain a steady concentration of NO in a spontaneous or continuous flow situation such as when a gas proportioner of gas blender is used. A differing use of that same algorithm may be used to achieve an instantaneous change in the NO/nitrogen supply flow to maintain the desired flow to the patient or, that same algorithm may be used to calculate a breath-by-breath flow of NO/nitrogen such that the flow from the gas delivery system may be determined and used to adjust the NO/nitrogen flow to maintain the desired NO concentration to the patient in the next breath delivered to the patient. In any manner, the CPU takes over the manual setting of any valves and established the concentration of NO to the patient as set or selected by the user.

Another use of the preferred signal processor, the CPU, is to supervise the safe operation of the NO delivery system by providing alarm functions and other functions to protect the patient in the event of faults in the delivery of NO.

As an alternate embodiment, a further means is included that adjusts the O2 concentration to the patient to compensate for the diminution of O2 to the patient as the patient inspiratory gas is loaded with NO/nitrogen to achieve a specified concentration of NO in the patients inspired gases. As a still further embodiment, a purge system is included that is activated to purge the various components and to fill the system with a gas having a known nitric oxide concentration from the supply.

The system also includes various controls, alarms and safety devices to prevent excess concentrations of $NO_2$ in the administration of NO to the patient, including means to shut down the NO system or to reduce the NO concentration to the patient to a safer level. The NO delivery system may thus provide an alarm or other appropriate action in the event of an increase in the NO level beyond a predetermined level, a decrease in O2 below a predetermined level and/or an increase of NO2 above a predetermined level. Depending on the severity of the alarm condition, an alarm may sound or the entire system may be controlled to alleviate the unsafe condition sensed.

These and other objects, features and advantages of the present invention will be more apparent from the detailed description of the preferred embodiment set forth below, taken in conjunction with the accompanying drawings.

DETAILED DESCRIPTION OF THE PREFERRED EMBODIMENTS

Figure 1:
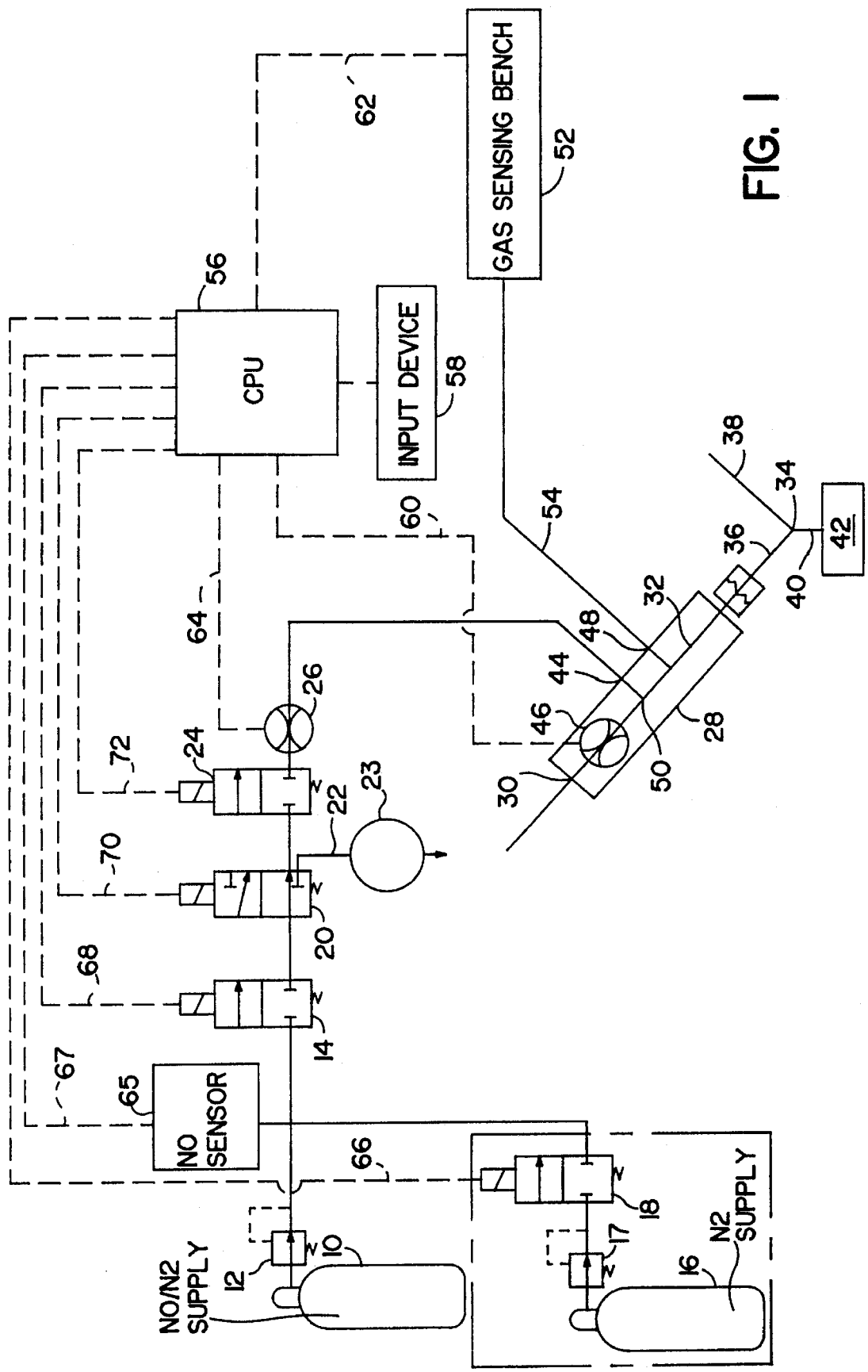
FIG. 1 is a schematic view, partially in block diagram form, of apparatus in accordance with an embodiment of the present invention.

Turning first to FIG. 1, there is shown a schematic view, partially in block diagram form, showing an apparatus constructed in accordance with the present invention. In the FIG. 1, a supply of nitric oxide is provided in the form of a cylinder 10 of gas. That gas is preferably nitric oxide mixed with nitrogen and is a commercially available mixture. Although the preferred embodiment utilizes the present commercial NO/nitrogen mixture, it is obvious that the NO may be introduced to the patient via some other gas, preferably an inert gas. Generally, of course, the cylinder 10 of nitric oxide is delivered pressurized and a typical pressure is on the order of about 2000 psi with a concentration of nitric oxide in the order of about 1000 ppm. Alternatively, the NO/nitrogen gas may be available in a central supply within a hospital and be available through the normal hospital piping system to various locations such as operating rooms. In such case, the pressure may already be reduced to a relatively lower amount that the cylinder pressures.

A pressure regulator 12 is used, therefore, to reduce the pressure of the gas in cylinder 10 down to acceptable levels for operation of the system, and again, typically, the regulator 12 reduces the pressure to about 40 psi or lower. An on-off shutoff valve 14 receives the reduced pressure gas from regulator 12 through a suitable conduit and is preferably solenoid operated. The use and purpose of the shutoff valve 14 will later be explained in conjunction with the operation of the nitric oxide delivery system.

A separate supply of pure nitrogen may be employed and, again, generally is provided by a cylinder 16 of nitrogen although pipeline nitrogen is available in numerous hospitals. The pressure of the nitrogen within cylinder 16 is reduced to the desired system level by means of regulator 17 and the nitrogen thereafter supplied via a conduit to a proportional control valve 18 that is controlled in a manner to be described. Suffice at this point is to state that the proportional control valve 18 provides a predetermined flow of nitrogen through a suitable conduit into the conduit to be mixed with the NO/nitrogen gas from cylinder 10 and which then enters the shutoff valve 14.

The purpose of the additional supply of nitrogen is to dilute, if necessary, the concentration of nitric oxide in the supply to the shutoff valve 14 to a desired amount. For example, the cylinder 10 may be supplying a concentration of nitric oxide that is too high for the particular flows in the system and therefore the concentration may be reduced to a more desirable level. If, of course, the supply of nitric oxide from cylinder 10 is suitable for the particular application, the addition of supplemental nitrogen is unnecessary.

Further downstream in the conduit carrying the NO/nitrogen stream is a purge valve 20 and which may be a solenoid operated valve that diverts the stream of NO/nitrogen from shutoff valve 14 to a sidestream 22 where the mixture is removed from the environment by means of a hospital evacuation or other system to remove such gases. Such system may, of course, have various treatment means such as a NO2 and NO scrubber 23 if required in a particular hospital.

Again, the control of the purge valve 20 and its use will be later explained in connection with the overall operation of the nitric oxide delivery system, and which is optional.

A further proportional control valve 24 is positioned with suitable conduit to receive the NO/nitrogen gas from the purge valve 20. Typical of such proportional control valves for both the proportional control valve 18 in the nitrogen supply system and the proportional control valve 24 in the NO/nitrogen stream may be obtained commercially from various companies, including MKS Instruments, Inc. of Andover, Mass. and which provide electronic control of gases. As may be seen, alternately, the valve may be a digital controlled valve rather that analog and which is controlled by timing its on/off cycles to effect the desired flow through the proportional control of flow therethrough. Combination of several valves used singly or in combination can be used to extend the delivery range.

A flow sensor 26 is located in the downstream conduit from proportional control valve 24 and senses the flow from such valve. Typically, in view of the values of flow at this point in the nitric oxide delivery system, the flow transducer may be of a technology such as the thermal mass flowmeter available from MKS Instruments, Inc. or may be of other technology of other suppliers.

A delivery adaptor 28 receives the NO/nitrogen gas via a suitable conduit for introduction into a further gas stream from the gas delivery system (not shown).

Delivery adaptor 28 is preferably a one piece reusable device and which has an inlet 30 which receives the gas delivered from the gas delivery system. As indicated, that gas delivery system may be a mechanical means providing a varying flow such as a ventilator, may be gas continuously supplied by a gas proportioning device for spontaneous ventilation or may be gases supplied to a bag for manual ventilation. As can be seen, the actual gas delivery system itself is not critical since the present system independently ascertains the flow from that system and proceeds to calculate and then deliver the proper flow of nitric oxide to arrive at the concentration to the patient that is selected by the user.

The delivery adaptor 28 has a main passage 32 therethrough and which receives the gas from the gas delivery device through inlet 30 for delivery to a patient. The gas actually delivered to the patient is transmitted via a patient wye piece 34 having an inspiratory limb 36 and an expiratory limb 38 of conventional design. The patient limb 40, obviously, leads to the patient indicated by the block 42.

A further inlet 44 is formed in the delivery adaptor 28 and which receives the NO/nitrogen gas from the proportional control valve 24 through flow sensor 26. As can be seen from FIG. 1, a flow transducer 46 is also included in the delivery adapter 28 and which detects the flow of gas from the gas delivery system. The inlet 44 is positioned downstream in the delivery adapter 28 from flow transducer 46. Flow transducer 46 may be of a variety of technologies, including pneumotach, hot wire anemometer, thermal flow sensor, variable orifice, thermal time-of-flight, rotating vane and the like. Included, obviously, are flow transducers that actually measure pressure, such as a pressure drop though an orifice, in order to determine flow.

A sampling port 48 is formed in the delivery adapter 28 and which communicates with the flow of gas passing through the main passage 32. It should be noted that the sampling port 48 thus samples the mixed gases, that is the gas downstream from the inlet 44 and thus downstream from a confluence 50 where the NO/nitrogen stream of gas is mixed with the inspiratory gas from the gas delivery system.

Accordingly, the flow from the gas delivery means enters the inlet 30 at a flow rate $Q_i$ and at a certain concentration of oxygen $\gamma O_{2i}$ and is mixed in the main passage of delivery adapter 28 with the NO/nitrogen gas from proportional control valve 24 at confluence 50. Flow transducer 46 is upstream of the confluence 50 and thus senses the flow only of the gas from the gas delivery system while sampling port 48 is downstream of the confluence 50 and thus provides access to samples of the gases that are mixed together at confluence 50. At confluence 50, there may be a diffuser such as a screen or sintered, porous block that enhances the mixing of the NO/nitrogen with the gases from the gas delivery system.

Therefore, the concentration of mixed gases at sampling port 48 contains the concentration of NO that actually enters the patient for therapeutic treatment and is the concentration set by the user, $\gamma NO_{set}$.

Connected to the gas sampling port 48 is a gas sensing bench 52 and which analyzes the concentrations of certain components of the gas stream administered to the patient. In the preferred embodiment, the gas sensing bench 52 samples the gases through conduit 54 and senses and quantifies the concentration of NO as well as NO2 and O2. Alternately, a sensor may be directly attached to the delivery adaptor 28 and directly sense such gas passing through the main passage 32.

A signal processing means, such as a CPU 56 is provided to solve certain equations and algorithms to operate the nitric oxide delivery system. CPU 56 receives a signal from an input device 58 indicative of the concentration the user desires to be administered to the patient. CPU 56 also receives signals from the flow transducer 46 indicative of the flow of gas delivered by the gas delivery system, $Q_i$ through a signal line 60 and also receives signals indicative of the concentration of NO, as well as $NO_2$ and $O_2$ from gas sensor bench 52 via a signal line 62 and a signal from flow sensor 26 indicative of the flow from proportional control valve 24, $Q_{del}$, respectively via a signal line 64.

Another input to CPU 56 is provided by the NO sensor 65 through signal line 67. The NO sensor 65 senses the concentration of NO in the supply cylinder 10 so that the user can verify that the proper supply is being utilized or, alternatively, the CPU 56 may use that input to adjust the system to adapt for any concentrations of NO in the supply within certain limits. NO sensor 65 could, of course, be eliminated if the NO cylinder 10 is always constant or by keying into the NO sensor in the gas sensing bench 52. A switching mechanism (not shown) would be required to sample from the multiple sources of samples.

Control signals are transmitted from CPU 56 to proportional control valve 18, shutoff valve 14, purge valve 20, and proportional valve 24 via signal lines 66, 68, 70, and 72 respectively.

In the operation of the present NO delivery system, therefore, the inlet 30 is connected to a gas delivery system, whether that gas delivery system is a mechanical ventilator or gas proportioning device or other means of supplying a breathing gas to a patient. As the gas is delivered from the gas delivery system, its flow is sensed by the flow transducer 46 in delivery adapter 28 and a signal is transmitted indicative of that flow to the CPU 56.

The user activates the input device 58 to select the desired concentration of NO that is to be administered to the patient. That input device 58 may be of a variety of devices, such as a keyboard, dial, encoder, touch screen, thumb wheel or the like. Alternatively, the input may be a signal that is built into the delivery system by the manufacturer and not be selectable by the actual end user. For example, the delivery system may be designed to operate to provide a fixed concentration of NO and the use of the system with any gas delivery system would result in that fixed, predetermined concentration of NO to be administered to the patient.

In the preferred embodiment, however, the desired NO concentration to be administered to the patient is set by the user by means of an input to CPU 56.

As can be seen, the CPU 56 has sufficient information to carry out the proper calculations, that is, it knows the flow of breathing gas from the gas delivery device by means of flow transducer 46 ($Q_i$) and the concentration of NO in the NO/nitrogen supply by means of NO sensor 65 ($\gamma_{NOcut}$). With that information, CPU 56 can calculate the desired flow ($Q_{del}$) from the proportional control valve 24 that needs to be provided to the confluence 50 to mix with the gas from the gas delivery system to produce the desired or set concentration ($\gamma_{NOset}$) established by the user through input device 58.

Basically, CPU 56 calculates the flow of NO/nitrogen to be added to the confluence 50 through the following equation;

$$Q_{del}(t) = [\gamma_{NOset}(t)/(\gamma_{NOcut} - \gamma_{NOset}(t)] * Q_i(t)$$

By this equation, the concentration of NO to the patient can be changed at an instantaneous rate limited only by the speed and sensitivity of the components such as flow transducer 46. The faster the response of flow transducer 46 is, the faster changes can be made in flow of the NO/nitrogen to confluence 50 by proportional control valve 24 such that the NO to the patient can instantaneously account for changes in the flow profile from the gas delivery system to maintain that concentration set by the user. The flow delivered ($Q_{del}$) from the proportional control valve 24 to the confluence 50 is determined from the concentration set by the user, ($\gamma NO_{set}$). The concentration $NO_{cut}$ is the concentration of NO in nitrogen from the supply cylinder 10 and the flow from the gas delivery system is $Q_i$. By this equation, the CPU 56 can make extremely rapid, such as 20 millisecond, changes to the flow delivered from proportional control valve 24 ($Q_{del}$) in order to maintain the concentration of the flow delivered to the patient at the desired level as determined by the user ($\gamma_{set}$).

As an alternate, the system may operate on a breath-by-breath basis, that is, the system can take a reading of the flow, or a portion thereof, from the gas delivery system at each breath and calculate the desired flow of NO/nitrogen for delivery at the next breath. Although such delivery is less rapid than the instantaneous equation, slower flow transducers and control valves may by employed and thus less expensive components used in the system. Therefore mean values can be used for the values set by the user ($\gamma_{NOset,mean}$) and the flow delivered by the proportional control valve 24 ($Q_{del}$) is expressed as a function of the inspired tidal volume of gas ($V_{t,insp}$) and the time of inspiration ($t_{insp}$). In such system, the equation is basically the same:

$$Q_{del} = [\gamma_{NOset,mean} / (\gamma_{NOcut} - \gamma_{NOset,mean})] * V_{t,insp} / t_{insp}.$$

With the breath-by-breath analysis, however, the flow transducer 46 may detect the start and end of a breath, or selected portion thereof, integrate to determine the total or fixed selected volume of the breath, and adjust the proportional control valve 24 to provide the set or desired concentration of NO at the next breath.

For constant or continuous flow ventilation from the gas delivery system as might be provided by a gas mixer or proportioning device, the same basic equation is used:

$$Q_{del} = [\gamma_{NOset} / (\gamma_{NOcut} - \gamma_{NOset})] * Q_i$$

In this case, however, since the flow is continuous and the tidal volume assure to be constant, the flow from the gas delivery system, ($Q_i$) may be sampled at a relatively slow rate, for example, once per second, and the flow of NO/nitrogen calculated and established from proportional control valve 24 on that particular timing cycle.

In any of the foregoing cases, the principal of operation is the same and the operative equation is basically the same. By knowing the flow from the gas delivery system by means of flow transducer 46 and the concentration of NO in the main supply from NO sensor 65, a derivation is made by the CPU 56 and the proportional control valve 24 is adjusted to provide then calculated flow of NO/nitrogen to arrive at the desired concentration set by the user in the breathing gas actually administered to the patient.

Confirmation of the flow from the proportional control valve 24 is made by the flow sensor 26 so that CPU 56 can check to see of the actual flow corresponds to the flow calculated and established by the CPU 56 through signal line 72 to proportional control valve 24. Alternatively, the flow sensor 26 can control the proportional control valve 24 using a feedback system and which is available in the commmercial valves from, for example, MKS Instruments Inc.

As is also be apparent from FIG. 1, CPU 56 also controls the proportional control valve 18 via signal line 66 and can operate that valve to further reduce the concentration of the NO in nitrogen from cylinder 10 in the event very low concentrations are set by the user and the system is otherwise unable to reduce the concentration to the desired point.

The gas sensing bench 52 provides a continuous monitor of the actual NO concentration administered to the patient and therefore is a further safety monitor. In the event the NO detected by the gas sensing bench 52 is a predetermined value away from the set point established by the user, an alarm may be triggered so the user can attend to the problem. In the event that the NO level rises to a dangerous level, CPU 56 will have that information and can take more drastic steps such as to discontinue use of the NO to the patient by shutting off the shutoff valve 14 or by automatically reducing the NO level to a lower, safe level established in the system.

As further alarms or triggers to actively change or terminate the NO system, the gas sensing bench 52 also monitors and provides the CPU 56 with a continuous reading of the concentrations of $O_2$ and $NO_2$ being administered to the patient and, again, the CPU 56 can be programmed to take the appropriate action, be it trigger an alarm or reduce the NO concentration in the event the $O_2$ level falls below a predetermined value or the $NO_2$ rises above a predetermined value.

Finally, in the event of a loss of pressure in the supply at any time, CPU 56 can activate purge valve 20 to purge the system of any other gases that may be in the supply line and refill the supply lines from cylinder 10 to the purge valve 20 with fresh NO/nitrogen. In this way, the system is recharged with the correct supply gas and no extraneous gases, such as ambient air, will be introduced into the system to cause error.

Accordingly, through the use of the present NO delivery system, the concentration of NO delivered to the patient may be established, either by the selection by the user, or set by a predetermined value by the system itself, and that desired value will be transmitted to the patient without any interrogation of the gas delivery device. The system is thus independent and may be readily used with any mechanical ventilator, gas proportioning device or other gas delivery system to deliver a known, desired concentration of NO to a patient.

Figure 2:
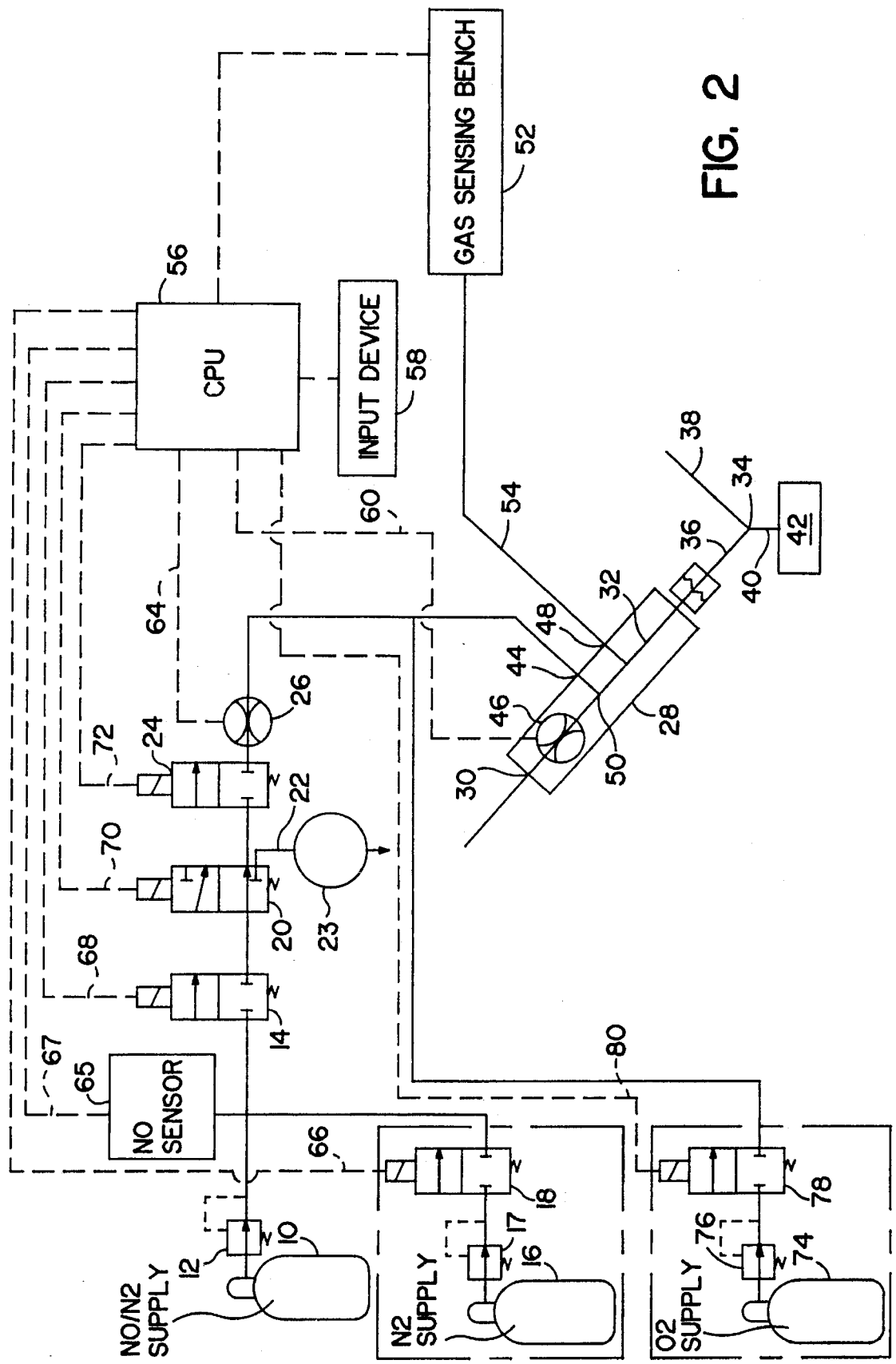
FIG. 2 is a schematic view, partially in block diagram from, of apparatus in accordance with another embodiment of the present invention.

Turning briefly to FIG. 2, there is shown in schematic view, partially in block form, of another embodiment of the present NO delivery system. In FIG. 2, all of the corresponding components have been numbered with the same identification numbers as in FIG. 1.

In this embodiment, however, an additional supplemental oxygen supply has been added by means of an oxygen cylinder 74 containing pressurized oxygen and which pressure is reduced by means of a regulator 76. Again it should be noted that the control of the oxygen supply is by means of a proportional control valve 78 which is controlled by the CPU 56 via a signal line 80.

Thus the operation of the FIG. 2 embodiment is the same as previously explained with respect to the FIG. 1 embodiment however the supplemental oxygen system may be used to add oxygen to the system in the event the gas sensing bench 52 indicates to the CPU 56 that the concentration of oxygen has been reduced to an unacceptable level. Such reduction in oxygen could occur in the event the concentration of NO is set to a very high level and the flow of NO/nitrogen from proportional control valve 24 to confluence 50 is very high and the combined flow to the patient thus is deprived of the needed amount of oxygen being supplied by the gas delivery system.

In such event, the CPU 56 merely signals proportional control valve 78 to add or increase the flow of oxygen to the NO/nitrogen stream being admitted to confluence 50, that is, upstream of confluence 50 by means of a suitable conduit Numerous further variations and combinations of the features discussed above can be utilized without departing from the spirit of the invention as defined by the claims. Accordingly, the foregoing description of the preferred embodiment should be taken by way of illustration rather than by way of limitation of the invention as claimed.

What is claimed is:

1. A nitric oxide delivery system for providing a predetermined concentration of nitric oxide to a patient, said nitric oxide delivery system having a connection means adapted to be fluidly connected to a supply of nitric oxide having a known concentration of nitric oxide, said nitric oxide delivery system further comprising a patient circuit having an inspiratory limb adapted to receive a breathing gas from a gas delivery system and communicate the breathing gas to a patient, a flow transducer located in said inspiratory limb of said patient breathing circuit for sensing the total flow of gas delivered by a gas delivery system to the patient and providing a signal indicative of such flow, input means for providing a signal indicative of the predetermined concentration of nitric oxide to be delivered to said inspirator limb of said breathing circuit, a flow control valve controlling the flow of nitric oxide from a supply of nitric oxide, conduit means in said inspiratory limb of said patient breathing circuit receiving the flow of nitric oxide from said flow control valve and combining the flow into the flow of gas from a gas delivery system, and a signal processor responsive to the signal from said flow transducer and to the signal indicative of the predetermined concentration to provide a signal to said flow control valve to establish a flow of nitric oxide through said flow control valve to said conduit means in an amount to establish a nitric oxide concentration delivered to a patient in the predetermined concentration.

2. A nitric oxide delivery system as defined in claim 1 wherein said conduit means combines the flow of the nitric oxide from a supply of nitric oxide and the flow of gas from a gas delivery system at a point downstream from said flow transducer.

3. A nitric oxide delivery system as defined in claim 1 wherein said means for providing a signal indicative of the predetermined nitric oxide concentration to be delivered to a patient comprises a control means operable by a user.

4. A nitric oxide delivery system as defined in claim 1 wherein said signal processor is a central processing unit (CPU).

5. A nitric oxide delivery system as defined in claim 4 wherein said means for providing a signal indicative of the predetermined nitric oxide concentration to be delivered to a patient comprises an electronic input device operable by a user to select said predetermined nitric oxide concentration and send an electrical signal to said CPU indicative of the selected concentration.

6. A nitric oxide delivery system as defined in claim 5 wherein said control valve is an electrically operated proportional control valve operable by an electrical signal from said CPU.

7. A nitric oxide delivery system as defined in claim 6 further including a sensor to detect at least the concentration of NO in the gas delivered to a patient.

8. A nitric oxide delivery system as defined in claim 1 further including a purge valve located in the path of flow of nitric oxide from a supply of nitric oxide, said purge valve being operable by said signal processor to purge said nitric oxide delivery system of other gases and to fill such system with nitric oxide from the supply of nitric oxide.

9. A nitric oxide delivery system for providing a predetermined concentration of nitric oxide to a patient, said system comprising a supply of nitric oxide having a known concentration, a gas delivery system for providing a breathing gas for delivery to a patient, said nitric oxide delivery system comprising a patient adapter receiving the breathing gas from said gas delivery system and connecting to a patient, said patient adapter having a passageway therethrough, a flow transducer within said patient adapter for sensing the total flow of breathing gas delivered by said gas delivery system and generating a signal indicative of such flow, control means for generating a signal indicative of the predetermined concentration of nitric oxide to be delivered to the patient from said patient adapter, a flow control valve controlling the flow of nitric oxide from said supply of nitric oxide, conduit means receiving the flow of the nitric oxide from said flow control valve and introducing the flow into said patient adapter, said flow of nitric oxide mixing within said patient adapter at a point downstream in said passageway from said flow transducer, and a signal processor responsive to the signal from said flow transducer representative of the sensed flow and to the signal from said control means to calculate and provide a signal to said flow control valve to establish a flow through said flow control valve to said patient adapter in an amount sufficient to establish a nitric oxide concentration delivered from said patient adapter to the patient in the predetermined amount.

10. A nitric oxide delivery system as defined in claim 9 wherein said patient adapter further includes a gas sensor adapted to sense the concentration of NO in the gas to be delivered to a patient.

11. A nitric oxide delivery system as defined in claim 10 wherein said signal processor is a central processing unit (CPU).

12. A nitric oxide delivery system as defined in claim 9 wherein said gas delivery system is a mechanical ventilator.

13. A nitric oxide delivery system as defined in claim 9 wherein said gas delivery system is a gas blender providing a continuous flow of gases.

14. A nitric oxide delivery system as defined in claim 9 wherein the gas is delivered to the patient through a wye piece and said patient adapter connects directly to the wye piece.

15. A method of providing a predetermined concentration of nitric oxide to a patient, said method comprising the steps of:

(a) providing a supply of pressurized nitric oxide gas of a known concentration, (b) providing a gas delivery system for delivering A flow of gas to a patient, (c) providing a patient breathing circuit having an inspiratory limb for receiving the flow of gas from the gas delivery system to deliver the flow of gas to a patient, (d) sensing the total flow of the gas delivered by the gas delivery system to a patient at a point in the inspiratory limb of the patient breathing circuit, (e) providing a signal indicative of the flow sensed in step (d), (f) providing a signal indicative of the predetermined concentration of nitric oxide to be delivered to a patient, (g) mixing a flow of gas from the gas delivery system and a flow of nitric oxide from the pressurized nitric oxide supply, (h) using the signals provided in steps (e) and (f) to control a flow of nitric oxide from the pressurized nitric oxide supply to establish a nitric oxide concentration delivered to the patient circuit in a predetermined amount.

16. A method as defined in claim 15 wherein said step of mixing the flow of gas from the gas delivery system and the flow of nitric oxide from the nitric oxide supply occurs at a point downstream in the flow toward the patient with respect to the point at which the flow of gas from the gas delivery system is sensed.

17. A method as defined in claim 15 wherein said step of providing a signal indicative of the predetermined concentration to be delivered to the patient comprises manually determining the signal by the user through an electronic input device.

18. A method as defined in claim 15 further including the step of:

(i) detecting the concentration of nitric oxide in the gas delivered to the patient.

19. A nitric oxide delivery system for providing a predetermined concentration of nitric oxide to a patient, said nitric oxide delivery system having a connection means adapted to be fluidly connected to a supply of nitric oxide of a known concentration, said nitric oxide delivery system further comprising an inspiratory conduit adapted to receive a breathing gas from a gas delivery system and communicate the breathing gas to a patient, a flow transducer for sensing the total flow of gas delivered by a gas delivery system through said inspiratory conduit to a patient and providing a signal indicative of such flow, an electronic input device operable by a user to select said predetermined nitric oxide concentration and to provide an electrical signal indicative of the predetermined concentration of nitric oxide to be delivered to a patient, an electrically operated proportional flow control valve controlling the flow of nitric oxide from a supply of nitric oxide, a mixing chamber within said inspiratory conduit receiving the flow of nitric oxide from said flow control valve and combining the flow into the flow of gas from a gas delivery system, a central processing unit (CPU) responsive to the signal from said flow transducer and to the electrical signal from said electronic input device indicative of the predetermined concentration to provide an electrical signal to operate said flow control valve to establish a flow of nitric oxide through said control valve to said conduit means in an amount to establish a nitric oxide concentration delivered to a patient in the predetermined amount and sensor means to detect the concentration of NO, $O_2$ and $NO_2$ in the gas delivered to a patient.

20. A nitric oxide delivery system for providing a predetermined concentration of nitric oxide to a patient, said system comprising a supply of nitric oxide having a known concentration, a mechanical ventilator for providing a plurality of breaths of varying flow of breathing gas for delivery to a patient, said nitric oxide delivery system comprising a flow transducer for sensing the flow of breathing gas delivered by said ventilator and generating a signal indicative of such flow, control means for generating a signal indicative of the predetermined concentration of nitric oxide to be delivered to the patient, a flow control valve controlling a flow of nitric oxide from said supply of nitric oxide, conduit means receiving the flow of the nitric oxide from said flow control valve and introducing the flow into the flow of gas from said ventilator, a central processing unit (CPU) responsive to the signal from said flow transducer representative of the sensed flow during each breath and said signal from said control means to calculate and provide a signal from said central processing unit to said flow control valve based on such calculation to establish a flow for the next succeeding breath through said flow control valve to said conduit means during each breath in an amount sufficient to establish a nitric oxide concentration delivered to the patient in the predetermined concentration.

21. A nitric oxide delivery system as defined in claim 20 wherein said CPU calculates the signal to the flow control valve based upon the following equation:

$$Q_{def} = [\gamma_{NOset,mean}/(\gamma_{NOcui} - \gamma_{NOset,mean})] * V_{t,insp}/t_{insp}.$$

22. A nitric oxide delivery system as defined in claim 21 wherein said CPU signals said flow control valve to establish the flow of nitric oxide from said flow control valve at predetermined time intervals.

23. A nitric oxide delivery system for providing a predetermined concentration of nitric oxide to a patient, said system comprising a supply of nitric oxide having a known concentration, a gas delivery system for providing a flow of breathing gas for delivery to a patient, said gas delivery system comprising a flow transducer for sensing the flow of breathing gas delivered by said gas delivery system and generating a signal indicative of such flow, control means for generating a signal indicative of the predetermined concentration of nitric oxide to be delivered to a patient, a flow control valve controlling a flow of nitric oxide from said supply of nitric oxide, conduit means receiving the flow of the nitric oxide from said flow control valve and introducing the flow into the flow of gas from said gas delivery system, a signal processor responsive to the signal from said flow transducer representative of the sensed flow and to the signal from said control means to provide a signal to said flow control valve to establish a flow through said flow control valve to said conduit means in an amount sufficient to establish a nitric oxide concentration delivered to a patient in the predetermined amount, said system further including a gas analyzing bench to analyze NO, $O_2$ and $NO_2$ in the stream of breathing gas delivered to the patient.

24. A nitric oxide delivery system as defined in claim 23 further including an alarm system operable by a signal from said signal processor indicative of the concentration of NO analyzed by said gas analyzing bench.

25. A nitric oxide delivery system for providing a predetermined concentration of nitric oxide to a patient, said nitric oxide delivery system having a patient circuit having an inspiratory limb adapted to be connected to a patient, a gas delivery system for supplying a breathing gas to a patient through said inspiratory limb of said patient circuit and having a supply of nitric oxide and a supply of an inert gas, said nitric oxide delivery system further comprising a flow transducer located in said inspiratory limb of said patient breathing circuit for sensing the flow of gas delivered by said gas delivery system to a patient and providing a signal indicative of such flow, means for providing a signal indicative of the predetermined concentration of nitric oxide to be delivered to said breathing circuit, a flow control valve controlling the flow of nitric oxide from said supply of nitric oxide, conduit means receiving the flow of the nitric oxide from said flow control valve and combining the flow into the flow of gas from said gas delivery system, a flow control valve controlling the flow of inert gas from said pressurized supply of inert gas and a signal processor responsive to the signal from said flow transducer and to the signal indicative of the predetermined concentration to provide a signal to said flow control valve to establish a flow of nitric oxide through said control valve to said conduit means in an amount to establish a predetermined nitric oxide concentration delivered to said patient breathing circuit and to provide a signal to said inert gas flow control valve to selectively add inert gas to said conduit means to reduce the concentration of nitric oxide delivered to the patient breathing circuit to attain a predetermined concentration of nitric oxide supplied to a patient.

26. A nitric oxide delivery system as defined in claim 25 wherein said inert gas is nitrogen.

27. A nitric oxide delivery system for providing a predetermined concentration of nitric oxide to a patient, said nitric oxide delivery system having a patient breathing circuit having an inspiratory limb adapted to be connected to a patient, a gas delivery system for supplying a breathing gas to a patient through said inspiratory limb of said patient circuit and having a pressurized supply of nitric oxide and a pressurized supply of oxygen, said nitric oxide delivery system further comprising a flow transducer located in said inspiratory limb of said patient breathing circuit for sensing the flow of gas delivered by a gas delivery system to a patient and providing a signal indicative of such flow, means for providing a signal indicative of the predetermined concentration of nitric oxide to be delivered to said patient breathing circuit, a flow control valve controlling the flow of nitric oxide from said supply of nitric oxide, a flow control valve controlling the flow of oxygen to be delivered to said patient breathing circuit, conduit means receiving the flow of nitric oxide from said flow control valve and combining the flow into the flow of gas from said gas delivery system, a flow control valve controlling the flow of oxygen from the pressurized supply of oxygen and a signal processor responsive to the signal from said flow transducer and to the signal indicative of the predetermined concentration of nitric oxide to provide a signal to said flow control valve to establish a flow of nitric oxide through said control valve to said conduit means in an amount to establish a predetermined nitric oxide concentration delivered to said patient breathing circuit and to provide a signal to said oxygen flow control valve to selectively add oxygen to said conduit means to prevent the concentration of oxygen delivered to a patient from becoming reduced below a predetermined level necessary for a patient.

* * * * *

(12) EX PARTE REEXAMINATION CERTIFICATE (9852nd)
United States Patent
Bathe et al.

(10) Number: US 5,558,083 C1
(45) Certificate Issued: Sep. 20, 2013

(54) NITRIC OXIDE DELIVERY SYSTEM

(75) Inventors: Duncan P. L. Bathe, Madison, WI (US);
Thomas S. Kohlmann, McFarland, WI (US); John R. Pinkert, Madison, WI (US); Robert Q. Tham, Middleton, WI (US)

(73) Assignee: Credit Suisse AG, Cayman Islands Branch, New York, NY (US)

Reexamination Request:
No. 90/012,311, Jun. 27, 2012

Reexamination Certificate for:
Patent No.: 5,558,083
Issued: Sep. 24, 1996
Appl. No.: 08/156,175
Filed: Nov. 22, 1993

(51) Int. Cl.
*A61M 16/10* (2006.01)

(52) U.S. Cl.
USPC ............. 128/203.12; 128/203.14; 128/203.25

(58) Field of Classification Search
None
See application file for complete search history.

(56) References Cited

To view the complete listing of prior art documents cited during the proceeding for Reexamination Control Number 90/012,311, please refer to the USPTO's public Patent Application Information Retrieval (PAIR) system under the Display References tab.

*Primary Examiner* — Catherine S. Williams

(57) ABSTRACT

A nitric oxide delivery system that is useable with any of a variety of gas delivery systems that provide breathing gas to a patient. The system detects the flow of gas delivered from the gas delivery system at various times and calculates the flow of a stream of nitric oxide in a diluent gas from a gas control valve. The flow of gas from the gas delivery system and the flow established from the flow control valve create a mixture having the desired concentration of nitric oxide for the patient.

The system does not have to interrogate the particular gas delivery system being used but is an independent system that can be used with various flows, flow profiles and the like from gas delivery systems.

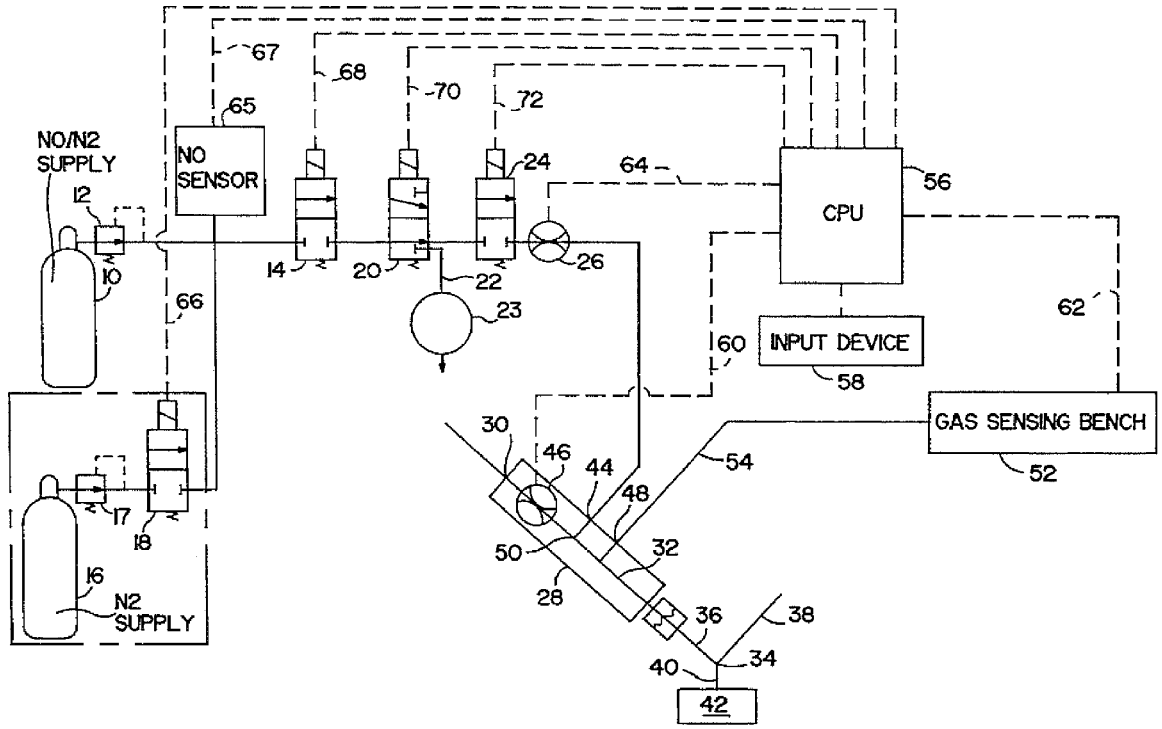

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-27 is confirmed.

* * * * *